United States Patent [19]
Takashima et al.

[11] Patent Number: 6,143,554
[45] Date of Patent: *Nov. 7, 2000

[54] PROCESS FOR PRODUCING OPTICALLY ACTIVE N-SUBSTITUTED AZETIDINE-2 CARBOXYLIC ACID COMPOUND

[75] Inventors: Yoshiki Takashima, Hyogo; Junko Kudo, Ibaraki; Ayumi Inoue, Nishinomiya; Motoo Hazama, Osaka, all of Japan

[73] Assignee: Sumitomo Chemical Company, Limited, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/352,350

[22] Filed: Jul. 13, 1999

[30] Foreign Application Priority Data

Jul. 17, 1998 [JP] Japan ................................. 10-203362

[51] Int. Cl.[7] ............................. C07C 1/04; C07D 205/04
[52] U.S. Cl. ............................................. 435/280; 548/953
[58] Field of Search ............................ 548/853; 435/280

[56] References Cited

U.S. PATENT DOCUMENTS

| | | | |
|---|---|---|---|
| 4,455,372 | 6/1984 | Chibata et al. | 435/107 |
| 5,879,929 | 3/1999 | Patel | 435/280 |
| 5,880,291 | 3/1999 | Ushio et al. | 548/953 |
| 5,942,630 | 8/1999 | Barth et al. | 548/953 |

FOREIGN PATENT DOCUMENTS

| | | |
|---|---|---|
| 0 855 446 A2 | 7/1998 | European Pat. Off. . |
| WO 98/02568 | 1/1998 | WIPO . |

OTHER PUBLICATIONS

Wim A. J. Starmans et al., "Enzymatic resolution of methyl N–alkyl–azetidine–2–carboxylates by *Candida antarCtica* lipase–mediated ammoniolysis", *Tetrehedron: Asymmetry*, vol. 9, 1998, pp. 429–435.

A. Kozikowski et al., "Synthesis and Metabotropic Receptor Activity of the Novel Rigidified Glutamate Analogues (+)–and (–)–trans–Azetidine–2,4–dicarboxylic Acid and Their N–Methyl Derivatives," *J. Med Chem.* (1993), 36, pp. 2706–2708.

*Primary Examiner*—Deborah C. Lambkin
*Attorney, Agent, or Firm*—Sughrue, Mion, Zinn, Macpeak & Seas, PLLC

[57] ABSTRACT

There is provided a process for producing an optically active N-substituted azetidine-2-carboxylic acid compound represented by the formula (2):

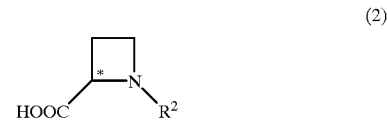

(2)

by contacting a corresponding N-substituted azetidine-2-carboxylic acid ester of formula (2) with an enzyme derived from a microorganism selected from Arthrobacter SC-6-98-28 strain, Arthrobacter sp. ATCC21908 strain, Chromobacterium SC-YM-1 strain, and a mutant thereof. A process is also provided for preparing an optically active azetidine-2-carboxylic acid by eliminating the N-substituent of a N-substituted azetidine-2-carboxylic acid ester of formula (2).

11 Claims, No Drawings

PROCESS FOR PRODUCING OPTICALLY ACTIVE N-SUBSTITUTED AZETIDINE-2 CARBOXYLIC ACID COMPOUND

BACKGROUND OF THE INVENTION

1. Field of the Invention

The present invention relates to a process for producing optically active N-substituted azetidine-2-carboxylic acid compounds and to a process for producing optically active azetidine-2-carboxylic acid, both of which are known as useful intermediates for producing pharmaceuticals and the like.

2. Description of Related Art

It has been known that the optically active N-substituted azetidine-2-carboxylic acid compounds and optically active azetidine-2-carboxylic acid were produced by an optical resolution method or a derivatization method from natural products.

As the optical resolution method, there can be mentioned, for example, a process in which benzyl DL-N-diphenylmethyl-azetidine-2-carboxylic acid ester is synthesized from γ-butyrolactone and reduced to DL-azetidine-2-carboxylic acid (R. M. Rodebaugh and N. H. Cromwell, Journal of Heterocyclic Chemistry, 6, 435–437 (1969)). Then an amino group of DL-azetidine-2-caboxylic acid is benzyloxycarbonylated and the resulting product is subjected to an optical resolution by allowing to form a salt with L-tyrosine hydrazide, followed by removal of the benzyloxycarbonyl group to give an optically active azetidine-2-carboxylic acid (R. M. Rodebaugh and N. H. Cromwell, Journal of Heterocyclic Chemistry, 6, 993–994 (1969)).

As the derivatization method from natural products, a method in which L-methionine, which is a starting material, is converted to L-N-tosyl-azetidine-2-carboxylic acid, from which the tosyl group is removed to produce optically active azetidine-2-carboxylic acid (Japanese Patent Kokai Publication No. 14457/1974) has been known.

These methods, however, have problems in that they require multiple steps and the yield was not always satisfactory. Therefore, the development of processes for producing optically active azetidine-2-carboxylic acid and optically active N-substituted azetidine-2-carboxylic acid compounds readily and in a good optical purity has been desired.

SUMMARY OF THE INVENTION

An object of the present invention is to provide a process for producing optically active N-substituted azetidine-2-carboxylic acid compounds in a single step in a good optical purity from N-substituted azetidine-2-carboxylic acid ester compounds by using specific enzymes, and another object is to provide a process for producing an optically active azetidine-2-carboxylic acid by eliminating the N-substituent.

The present invention provides:

1. A process for producing an optically active N-substituted azetidine-2-carboxylic acid compound represented by the formula (1):

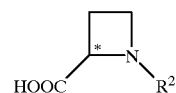

(1)

wherein $R^2$ represents:

an aralkyl group, which may be substituted on its aromatic ring with at least one group selected from an alkyl group having 1 to 8 carbon atoms, an alkoxy group having 1 to 8 carbon atoms, a halogen atom and a nitro group, or an alkylcarbonyl group having 1 to 8 carbon atoms, which may be substituted with at least one group selected from an alkoxy group having 1 to 8 carbon atoms, a halogen atom and a nitro group, or an arylcarbonyl group, which may be substituted on its aromatic ring with at least one group selected from an alkyl group having 1 to 8 carbon atoms, an alkoxy group having 1 to 8 carbon atoms, a halogen atom, a phenyl group and a nitro group, or an alkyloxycarbonyl group having 1 to 8 carbon atoms, which may be substituted with at least one group selected from a halogen atom, a sulfonyl group and an aryl group, which aryl group may be substituted on its aromatic ring with at least one group selected from an alkyl group having 1 to 8 carbon atoms, an alkoxy group having 1 to 8 carbon atoms, a halogen atom and a nitro group, or an allyloxycarbonyl group, or an aryloxycarbonyl group, which may be substituted on its aromatic ring with at least one group selected from an alkyl group having 1 to 8 carbon atoms, an alkoxy group having 1 to 8 carbon atoms, a halogen atom and a nitro group, or an alkyl group having 1 to 8 carbon atoms, which may be substituted with at least one group selected from an alkoxy group having 1 to 8 carbon atoms, a halogen atom and a nitro group, or an allyl group, or an aryl group, which may be substituted on its aromatic ring with at least one group selected from an alkyl group having 1 to 8 carbon atoms, an alkoxy group having 1 to 8 carbon atoms, a halogen atom and a nitro group, or an arylsulfonyl group, which may be substituted on its aromatic ring with at least one group selected from an alkyl group having 1 to 8 carbon atoms, an alkoxy group having 1 to 8 carbon atoms, a halogen atom and a nitro group, and

* represents an asymmetric carbon atom, the process comprising asymmetrically hydrolyzing an N-substituted azetidine-2-carboxylic acid ester compound represented by the formula (2):

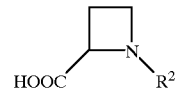

(2)

wherein $R^1$ represents:

an alkyl group having 1 to 8 carbon atoms, which may be substituted with at least one group selected from an alkoxy group having 1 to 8 carbon atoms, a halogen atom and a nitro group, or an allyl group, or an aralkyl group, which may be substituted on its aromatic ring with at least one group selected from an alkyl group having 1 to 8 carbon atoms, an alkoxy group having 1 to 8 carbon atoms, a halogen atom and a nitro group, or an aryl group, which may be substituted on its aromatic ring with at least one group selected from an alkyl group having 1 to 8 carbon atoms, an alkoxy group having 1 to 8 carbon atoms, a halogen atom and a nitro group and $R^2$ has the same meaning as defined above, by contacting the same with an enzyme derived from a microorganism selected from Arthrobacter SC-6-98-28 strain, Arthrobacter sp. ATCC21908 strain, Chromobacterium SC-YM-1 strain and a mutant thereof; and 2. A process for producing optically active azetidine-2-carboxylic acid represented by the formula (3):

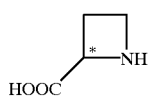

(3)

wherein * has the same meaning as defined above, the process being characterized by eliminating the N-substituent of the optically active N-substituted azetidine-2-carboxylic acid compounds represented by the formula (1) obtained above.

DETAILED DESCRIPTION OF THE INVENTION

The present invention will be described in detail below.

In the N-substituted azetidine-2-carboxylic acid ester compounds represented by the formula (2), examples of the N-substituent represented by $R^2$ include, for example;

an aralkyl group which may be substituted, on its aromatic ring, with at least one group selected from an alkyl group having 1 to 8 carbon atoms, an alkoxy group having 1 to 8 carbon atoms, a halogen atom and a nitro group (e.g., a benzyl group, a p-chlorobenzyl group, α-phenylethyl group, a β-phenylethyl group, a phenylpropyl group, a benzhydryl group and a triphenylmethyl group); or an acyl group such as an alkylcarbonyl group having 1 to 8 carbon atoms which may be substituted with at least one group selected from an alkoxy group having 1 to 8 carbon atoms, a halogen atom and a nitro group, (e.g. an acetyl group, a chloroacetyl group and a trifluoroacetyl group) and an arylcarbonyl group which may be substituted, on its aromatic ring, with an alkyl group having 1 to 8 carbon atoms, an alkoxy group having 1 to 8 carbon atoms, a halogen atom, a phenyl group and a nitro group (e.g. a benzoyl group and a p-phenylbenzoyl group); or an alkyloxycarbonyl group having 1 to 8 carbon atoms, which alkyl group may be substituted with at least one group selected from a halogen atom, a sulfonyl group (e.g., C1–C8 alkyl sulfonyl group or arylsulfonyl group) and an aryl group, which aryl group may be substituted on its aromatic ring with at least one group selected from an alkyl group having 1 to 8 carbon atoms, an alkoxy group having 1 to 8 carbon atoms, a halogen atom and a nitro group, such as a t-butoxycarbonyl group, a trichloroethyloxycarbonyl group, a benzyloxycarbonyl group, a p-nitrobenzyloxycarbonyl group and a 2-phenylethyloxycarbonyl group; or an allyloxycarbonyl group; or an aryloxycarbonyl group which may be substituted, on its aromatic ring, with at least one group selected from an alkyl group having 1 to 8 carbon atoms, an alkoxy group having 1 to 8 carbon atoms, a halogen atom and a nitro group, such as a 2, 4, 6-tri-t-butylphenyloxycarbonyl group; or an alkyl group having 1 to 8 carbon atoms which may be substituted with at least one group selected from an alkoxy group having 1 to 8 carbon atoms, a halogen atom and a nitro group, such as a methyl group, an ethyl group, a n-propyl group, an isopropyl group, a n-butyl group, an isobutyl group, a sec-butyl group, a t-butyl group; or an allyl group; or an aryl group which may substituted, on its aromatic ring, with at least one group selected from an alkyl group having 1 to 8 carbon atoms, an alkoxy group having 1 to 8 carbon atoms, a halogen atom and a nitro group, such as a phenyl group; or an arylsulfonyl group which may be substituted, on its aromatic ring, with at least one group selected from an alkyl group having 1 to 8 carbon atoms, an alkoxy group having 1 to 8 carbon atoms, a halogen group and a nitro group, such as a p-toluenesulfonyl group, a benzenesulfonyl group, a methoxybenzenesulfonyl group and a nitrobenzenesulfonyl group.

Such substituents may have an asymmetric carbon atom. As such an N-substituent represented by $R^2$ having the asymmetric carbon atom, there can be mentioned, for example, an (S)-phenylethyl group and an (R)-phenylethyl group.

Examples of the alkyl group represented by Rinclude:

an alkyl group having 1 to 8 carbon atoms which may be substituted with at least one group selected from an alkoxy group having 1 to 8 carbon atoms, a halogen atom and a nitro group, such as a methyl group, an ethyl group, a n-propyl group, an isopropyl group, a n-butyl group, an isobutyl group, a sec-butyl group, a t-butyl group; or an aralkyl group which may be substituted, on its aromatic ring, with at least one group selected from an alkyl group having 1 to 8 carbon atoms, an alkoxy group having 1 to 8 carbon atoms, a halogen atom and a nitro group, such as a benzyl group, a p-chlorobenzyl group, an α-phenylethyl group, a β-phenylethyl group, a phenylpropyl group, benzhydryl group and a triphenylmethyl group; or an allyl group; or an aryl group which may be substituted, on its aromatic ring, with at least one group selected from an alkyl group having 1 to 8 carbon atoms, an alkoxy group having 1 to 8 carbon atoms, a halogen atom and a nitro group, such as a phenyl group.

In $R^1$ or $R^2$, the aralkyl group means a C1–C3 alkyl group substituted with 1 to 3 aryl groups, aromatic ring of which may be substituted, and the aryl group for the arylcarbonyl, aryloxycarbonyl, aryl, arylsulfonyl or aralkyl group means a phenyl group or a naphthyl group, and preferably a phenyl group.

Examples of such N-substituted azetidine-2-carboxylic acid ester compounds include:

methyl N-benzylazetidine-2-carboxylic acid ester,
methyl N-p-chlorobenzylazetidine-2-carboxylic acid ester,
methyl N-[(S)-phenylethyl]-azetidine-2-carboxylic acid ester,
methyl N-[(R)-phenylethyl]-azetidine-2-carboxylic acid ester,
methyl N-β-phenylethylazetidine-2-carboxylic acid ester,
methyl N-phenylpropylazetidine-2-carboxylic acid ester,
methyl N-benzhydrylazetidine-2-carboxylic acid ester,
methyl N-triphenylmethylazetidine-2-carboxylic acid ester,
methyl N-acetylazetidine-2-carboxylic acid ester,
methyl N-chloroacetylazetidine-2-carboxylic acid ester,
methyl N-trifluoroacetylazetidine-2-carboxylic acid ester,
methyl N-benzoylazetidine-2-carboxylic acid ester,
methyl N-p-phenylbenzoylazetidine-2-carboxylic acid ester,
methyl N-t-butoxycarbonylazetidine-2-carboxylic acid ester,
methyl N-trichloroethyloxycarbonylazetidine-2-carboxylic acid ester,
methyl N-benzyloxycarbonylazetidine-2-carboxylic acid ester,
methyl N-p-nitrobenzyloxycarbonylazetidine-2-carboxylic acid ester,
methyl N-2-phenylethyloxycarbonylazetidine-2-carboxylic acid ester,
methyl N-allyloxycarbonylazetidine-2-carboxylic acid ester,
methyl N-2, 4, 6-tri-t-butylphenyloxycarbonylazetidine-2-carboxylic acid ester,
methyl N-methylazetidine-2-carboxylic acid ester,
methyl N-ethylazetidine-2-carboxylic acid ester,
methyl N-n-propylazetidine-2-carboxylic acid ester,
methyl N-isopropylazetidine-2-carboxylic acid ester,
methyl N- n-butylazetidine- 2-carboxylic acid ester,
methyl N-iso butylazetidine-2-carboxylic acid ester,
methyl N-sec-butylazetidine-2-carboxylic acid ester,
methyl N-t-butylazetidine-2-carboxylic acid ester,
methyl N-allylazetidine-2-carboxylic acid ester,
methyl N-phenylazetidine-2-carboxylic acid ester,
methyl N-p-toluenesulfonylazetidine-2-carboxylic acid ester,
methyl N-benzenesulfonylazetidine-2-carboxylic acid ester,
methyl N-methoxybenzenesulfonylazetidine-2-carboxylic acid ester,
methyl N-nitrobenzenesulfonylazetidine-2-carboxylic acid ester, and an ethyl, a n-propyl, an isopropyl, a n-butyl, an isobutyl, a sec-butyl, a t-butyl, a benzyl, an (S)-phenylethyl, an (R)-phenylethyl, a β-phenylethyl, a phenylpropyl, a benzhydryl, a triphenylmethyl, an allyl, a phenyl and a naphthyl ester corresponding to the above-listed methyl esters.

Each of the N-substituted azetidine-2-carboxylic acid ester compounds represented by the formula (2) may include two optical isomers resulting from an asymmetric carbon atom which corresponds to an asymmetric carbon atom designated by * in the formula (1) as an asymmetric center.

The N-substituted azetidine-2-carboxylic acid ester compounds represented by the formula (2) to be used in the present invention may either be a racemic mixture of both of the optical isomers in the same amount or contain an excess amount of one optical isomer.

Examples of the enzyme capable of asymmetrically hydrolyzing the N-substituted azetidine-2-carboxylic acid ester compounds represented by the formula (2) include enzymes derived from microorganisms such as Arthrobacter SC-6-98-28 strain (FERM BP-3658), Arthrobacter sp. ATCC21908 strain, Chromobacterium SC-YM-1 strain (FERM BP-6703), and enzymes derived from a mutant derived from the above microorganisms by means of a mutagenic agent or ultraviolet ray, enzymes produced by a recombinant microorganism transformed by introduction of the enzyme gene contained in the above microorganisms, enzymes obtained by substituting the specific amino acids in the amino acid sequence of the above enzymes with at least one other amino acid using a usual gene engineering technique, etc.

More specifically, the esterase derived from Arthrobacter SC-6-98-28 strain (FERM BP-3658) which is prepared by the known method described in Japanese Patent Kokai Publication No. 56787/1993, the esterase derived from Chromobacterium SC-YM-1 strain (FERM BP-6703) which is prepared by the known method described in Japanese Patent Kokai Publication No. 163364/1995, the heat-resistant esterase obtained by a site-specific amino acid substitution which is prepared by the method described in Japanese Patent Kokai Publication No. 213280/1995, etc are preferably used.

Among these, particularly in the case of using the esterase derived from Arthrobacter SC-6-98-28 strain (FERM BP-3658), a good optical selectivity can be attained in the asymmetric hydrolysis of the N-substituted azetidine-2-carboxylic acid ester compound represented by the formula (2) and the R isomer of the N-substituted azetidine-2-carboxylic acid represented by the formula (1) can be obtained in a good optical purity.

Purity and form of the enzymes to be used are not particularly limited, and the enzymes can be used in various forms, for example, in a form of purified enzyme, crude enzyme, culture broth of microorganism, cells of microorganism and treated products thereof. Asymmetrical hydrolysis of the N-substituted azetidine-2-carboxylic acid ester compound of the formula (2) is usually conducted by contacting the ester compound of the formula (2) with the enzyme in a form of purified enzyme, crude enzyme, culture broth of microorganism, cells of microorganism or treated products thereof.

The above treated product means, for example, a freeze-dried cells of microorganism, an acetone-dried cells of microorganism, a disruption product of cells of microorganism, an autolysate of cells of microorganism, an ultrasonication product of cells of microorganism, a cell-free extract and an alkali-treated product. In addition, the enzymes having various purity and forms also may be employed by immobilizing by means of known methods such as the adsorption method in which the enzyme is adsorbed to an inorganic support such as silica gel and ceramics or to cellulose or to an ion exchange resin, the polyacrylamide method, the sulfur-containing polysaccharide gel method (for example, the carragreenan gel method), the alginic acid gel method and the agarose gel method.

Culture of microorganisms for producing the enzymes can be readily carried out by means of conventional methods. As a medium, there can be utilized a variety of mediums optionally containing a carbon source, a nitrogen source, an inorganic compound and so on which are conventionally employed for culture of microorganisms. Examples of the carbon sources include glucose, glycerine, organic acids, molasses and the like. Examples of the nitrogen sources include peptone, yeast extract, malt extract, soybean powder, corn steep liquor, cotton-seed powder, dried yeast, casamino acid, ammonium chloride, ammonium nitrate, ammonium sulfate, urea and the like. Examples of the inorganic compounds include chlorides, sulfates and phosphates of potassium, sodium, magnesium, iron, manganese, cobalt, zinc and the like, specifically, potassium chloride, sodium chloride, magnesium sulfate, ferrous sulfate, manganese sulfate, cobalt chloride, zinc sulfate, potassium phosphate, sodium phosphate and the like. Additionally, in order to increase the ability of the microorganisms to asymmetrically hydrolyze N-substituted azetidine-2-carboxylic acid ester compounds, triglycerides such as olive oil, tributyrin may optionally be added to the medium.

In general, the culture of microorganisms is preferably carried out aerobically by liquid culture. It is preferred that the microorganism is inoculated onto the above sterilized culture medium, and subjected to shaking culture or aerobic culture with stirring. The culture temperature is usually 20° C. to 40° C., preferably 25° C. to 35° C. The pH value is preferably 6 to 8. The culture time varies depending on various conditions, but is preferably about 1 to 7 days.

A solid culture method, if desired, also can be optionally adopted as long as the method can produce a microorganism cells capable of asymmetrically hydrolyzing the N-substituted azetidine-2-carboxylic acid ester compounds.

Such an enzyme is adequately chosen depending on the desired optically active N-substituted azetidine-2-carboxylic acid compound represented by the formula (1). The amount of the enzyme to be used is optionally set in a range within which deferring of the reaction should not occur or the selectivity of the reaction should not lower. For example, in the case that a commercially available enzyme is used, the amount thereof is 0.001 to 50 parts by weight, preferably 0.002 to 20 parts by weight per part by weight of the N-substituted azetidine-2-carboxylic acid ester compound.

The asymmetric hydrolysis reaction of the N-substituted azetidine-2-carboxylic acid ester compounds represented by the formula (2) using the enzyme is usually carried out in the presence of water, which may be an aqueous buffer solution. Examples of the buffer solution include those of inorganic acid salts such as aqueous solutions of alkali metal phosphate salts (e.g., an aqueous sodium phosphate solution and an aqueous potassium phosphate solution) and those of organic acid salts such as aqueous solutions of alkali metal acetate (e.g., an aqueous sodium acetate solution and an aqueous potassium acetate solution).

The amount of water to be used may usually be not less than 0.5 mole per mole of the N-substituted azetidine-2-carboxylic acid ester compound represented by the formula (2). Although, in some cases, water is used in such amount that it serves as a solvent, it is generally used in an amount of not more than 100 parts by weight per part by weight of the N-substituted azetidine-2-carboxylic acid ester compound.

The asymmetric hydrolysis reaction may be carried out in the presence of organic solvents such as a hydrophobic organic solvent and a hydrophilic organic solvent, in addition to the above water or aqueous buffer solution.

Examples of the hydrophobic organic solvent include ether such as t-butyl methyl ether and isopropyl ether, hydrocarbons such as toluene, hexane, cyclohexane, heptane and isooctane. Examples of the hydrophilic organic solvent include alcohol such as t-butanol, methanol, ethanol, isopropanol and n-butanol, ether such as tetrahydrofuran, sulfoxide such as dimethyl sulfoxide, ketone such as acetone, nitrile such as acetonitrile. The hydrophobic organic solvent and hydrophilic organic solvent are, respectively, used alone or as a mixture containing two or more thereof. Alternatively, the hydrophobic organic solvent and hydrophilic organic solvent may be used in combination.

When the organic solvent is used, the amount of the solvent to be used is usually not more than 100 parts by weight, preferably within a range of 0.1 to 50 parts by weight per 1 part by weight of the N-substituted azetidine-2-carboxylic acid ester compound represented by the formula (2).

The asymmetric hydrolysis reaction is carried out, for example, by a method in which water, an N-substituted azetidine-2-carboxylic acid ester compound and an enzyme are mixed. In the case that an organic solvent is used, water, the N-substituted azetidine-2-carboxylic acid ester compound and the enzyme may be mixed in the organic solvent. The enzyme may be used in an immobilized form to a resin.

The pH of the reaction system is not particularly limited and optionally selected so that the asymmetric hydrolysis reaction can proceed in a high selectivity. In general, the pH falls within a range of from 4 to 10.

Because an excessively high reaction temperature tends to deteriorate stability of the enzyme and an excessively low reaction temperature tends to decrease the reaction rate, the reaction temperature is usually within the range of from 5° C. to 65° C., preferably from 20° C. to 50° C.

In the asymmetric hydrolysis, one optical isomer of the N-substituted azetidine-2-carboxylic acid ester compound represented by the formula (2) is preferentially hydrolyzed with retention of the configuration at the asymmetric carbon atom marked with * in the formula (2) to produce the desired optically active N-substituted azetidine-2-carboxylic acid compound represented by the formula (1).

A treatment after completion of the hydrolysis is usually carried out by, if necessary adding a hydrophobic organic solvent and/or water and, separating the mixture into an aqueous layer and an organic layer. By this operation, an aqueous solution of the desired optically active N-substituted azetidine-2-carboxylic acid compound represented by the formula (1) can be obtained. In the case that insoluble substances are contained in the reaction solution, for example, in the case that an enzyme immobilized to a resin or the like is used, the above separation operation may be carried out after removing the insoluble substances by filtration or the like.

Examples of the hydrophobic organic solvent which can be used in this operation include ether such as t-butyl methyl ether and isopropyl ether, hydrocarbons such as toluene, hexane, cyclohexane, heptane and isooctane, halogenated hydrocarbons such as dichloromethane, dichloroethane, chloroform, chlorobenzene and orthodichlorobenzene, and esters such as ethyl acetate, methyl acetate and butyl acetate. As in the organic layer obtained by this operation is contained the N-substituted azetidine-2-carboxylic acid ester compound represented by the formula (2) as an asymmetric hydrolysis residue, this can produce, by means of a usual hydrolysis using acid, alkali or the like, the N-substituted azetidine-2-carboxylic acid compound represented by the formula (1) having the opposite configuration of the compound obtained above.

The aqueous solution of the optically active N-substituted azetidine-2-carboxylic acid compound represented by the formula (1) obtained by the above asymmetric hydrolysis reaction using the enzyme can be employed as a raw material of the optically active azetidine-2-carboxylic acid represented by the formula (3) in the next step without any treatment. According to demand, the optically active N-substituted azetidine-2-carboxylic acid compound represented by the formula (1) can be isolated by concentrating the solution thereof. The obtained optically active N-substituted azetidine-2-carboxylic acid compound represented by the formula (1) may be further purified by recrystallization, column chromatography or the like, if necessary.

Examples of the thus obtained optically active N-substituted azetidine-2-carboxylic acid compound represented by the formula (1) include:
(2S)-N-benzylazetidine-2-carboxylic acid,
(2S)-N-p-chlorobenzylazetidine-2-carboxylic acid,
(2S)-N-[(S)-phenylethyl]-azetidine-2-carboxylic acid,
(2S)-N-[(R)-phenylethyl]-azetidine-2-carboxylic acid,
(2S)-N-β-phenylethylazetidine-2-carboxylic acid,
(2S)-N-phenylpropylazetidine-2-carboxylic acid,
(2S)-N-benzhydrylazetidine-2-carboxylic acid,
(2S)-N-triphenylmethylazetidine-2-carboxylic acid,
(2S)-N-acetylazetidine-2-carboxylic acid,
(2S)-N-chloroacetylazetidine-2-carboxylic acid,
(2S)-N-trifluoroacetylazetidine-2-carboxylic acid,
(2S)-N-benzoylazetidine-2-carboxylic acid,
(2S)-N-p-phenylbenzoylazetidine-2-carboxylic acid,
(2S)-N-t-butoxycarbonylazetidine-2-carboxylic acid,
(2S)-N-trichloroethyloxycarbonylazetidine-2-carboxylic acid,
(2S)-N-benzyloxycarbonylazetidine-2-carboxylic acid,
(2S)-N-p-nitrobenzyloxycarbonylazetidine-2-carboxylic acid,
(2S)-N-2-phenylethyloxycarbonylazetidine-2-carboxylic acid,
(2S)-N-allyloxycarbonylazetidine-2-carboxylic acid,
(2S)-N-2, 4, 6-tri-t-butylphenyloxycarbonylazetidine-2-carboxylic acid,
(2S)-N-methylazetidine-2-carboxylic acid,
(2S)-N-ethylazetidine-2-carboxylic acid,
(2S)-N-n-propylazetidine-2-carboxylic acid,
(2S)-N-isopropylazetidine-2-carboxylic acid,
(2S)-N-n-butylazetidine-2-carboxylic acid,
(2S)-N-isobutylazetidine-2-carboxylic acid,
(2S)-N-sec-butylazetidine-2-carboxylic acid,
(2S)-N-t-butylazetidine-2-carboxylic acid,
(2S)-N-allylazetidine-2-carboxylic acid,
(2S)-N-phenylazetidine-2-carboxylic acid,
(2S)-N-p-toluenesulfonylazetidine-2-carboxylic acid,
(2S)-N-benzenesulfonylazetidine-2-carboxylic acid,
(2S)-N-methoxybenzenesulfonylazetidine-2-carboxylic acid,
(2S)-N-nitrobenzenesulfonylazetidine-2-carboxylic acid,
(2R)-N-benzylazetidine-2-carboxylic acid,
(2R)-N-p-chlorobenzylazetidine-2-carboxylic acid,
(2R)-N-[(S)-phenylethyl]-azetidine-2-carboxylic acid,
(2R)-N-[(R)-phenylethyl]-azetidine-2-carboxylic acid,
(2R)-N-β-phenylethylazetidine-2-carboxylic acid,
(2R)-N-phenylpropylazetidine-2-carboxylic acid,
(2R)-N-benzhydrylazetidine-2-carboxylic acid,
(2R)-N-triphenylmethylazetidine-2-carboxylic acid,
(2R)-N-acetylazetidine-2-carboxylic acid,
(2R)-N-chloroacetylazetidine-2-carboxylic acid,
(2R)-N-trifluoroacetylazetidine-2-carboxylic acid,
(2R)-N-benzoylazetidine-2-carboxylic acid,
(2R)-N-p-phenylbenzoylazetidine-2-carboxylic acid,
(2R)-N-t-butoxycarbonylazetidine-2-carboxylic acid,
(2R)-N-trichloroethyloxycarbonylazetidine-2-carboxylic acid,
(2R)-N-benzyloxycarbonylazetidine-2-carboxylic acid,
(2R)-N-p-nitrobenzyloxycarbonylazetidine-2-carboxylic acid,
(2R)-N-2-phenylethyloxycarbonylazetidine-2-carboxylic acid,
(2R)-N-allyloxycarbonylazetidine-2-carboxylic acid,
(2R)-N-2, 4, 6-tri-t-butylphenyloxycarbonylazetidine-2-carboxylic acid,
(2R)-N-methylazetidine-2-carboxylic acid,
(2R)-N-ethylazetidine-2-carboxylic acid,
(2R)-N-n-propylazetidine-2-carboxylic acid,
(2R)-N-isopropylazetidine-2-carboxylic acid,
(2R)-N-n-butylazetidine-2-carboxylic acid,
(2R)-N-isobutylazetidine-2-carboxylic acid,
(2R)-N-sec-butylazetidine-2-carboxylic acid,
(2R)-N-t-butylazetidine-2-carboxylic acid,
(2R)-N-allylazetidine-2-carboxylic acid,
(2R)-N-phenylazetidine-2-carboxylic acid,
(2R)-N-p-toluenesulfonylazetidine-2-carboxylic acid,
(2R)-N-benzenesulfonylazetidine-2-carboxylic acid,
(2R)-N-methoxybenzenesulfonylazetidine-2-carboxylic acid, and
(2R)-N-nitrobenzenesulfonylazetidine-2-carboxylic acid, etc.

The optically active azetidine-2-carboxylic acid represented by the formula (3) can be produced by the removal of the N-substituent of the optically active N-substituted azetidine-2-carboxylic acid compound represented by the formula (1).

When the substituent $R^2$ is the aralkyl group, which may be substituted on its aromatic ring with at least one group selected from an alkyl group having 1 to 8 carbon atoms, an alkoxy group having 1 to 8 carbon atoms, a halogen atom and a nitro group, or an alkyloxycarbonyl group having 1 to 2 carbon atom which is substituted with an aryl group, which may be substituted on its aromatic ring with at least one group selected from an alkyl group having 1 to 8 carbon atoms, an alkoxy group having 1 to 8 carbon atoms, a halogen atom and a nitro group, removal of the substituent $R^2$ is usually conducted by reacting such a compound in the presence of a catalyst, with a reducing agent to produce the optically active azetidine-2-carboxylic acid represented by the formula (3).

The catalyst may be, for example, noble metal catalysts usually employed in a catalytic hydrogenation reaction, more specifically palladium, palladium acetate, palladium chloride, palladium oxide, palladium hydroxide and the like, which may be supported on activated carbon, alumina and the like. The amount of the catalyst to be used is usually within a range of from 0.0001 to 0.5 part by weight per 1 part by weight of the optically active N-substituted azetidine-2-carboxylic acid compound represented by the formula (1).

Examples of the reducing agent include hydrogen, hydrazine and a salt thereof such as a hydrochloride, a sulfate, an acetate and the like, and formic acid and an ammonium salt thereof.

The reaction is usually carried out in a solvent. Examples of the solvent include: water, an alcohol solvent such as methanol, ethanol and 2-propanol, an ester solvent such as ethyl acetate, methyl acetate and butyl acetate, a nitrile solvent such as acetonitrile, an aromatic hydrocarbon solvent such as toluene, xylene and benzene, an aliphatic hydrocarbon solvent such as hexane and heptane, a halogen-containing hydrocarbon solvent such as dichloromethane, dichloroethane, chloroform, chlorobenzene and orthodichlorobenzene, an ether solvent such as diethyl ether, isopropyl ether and t-butyl methyl ether, an amide solvent such as acetamide, N, N-dimethyl formamide and N, N-dimethylacetamide. These solvents may be used alone or in combination of two or more. The amount of the solvent to be used is usually within a range of from 2 to 100 parts by weight per part by weight of the optically active N-substituted azetidine-2-carboxylic acid compound represented by the formula (1).

When hydrogen is employed as a reducing agent, for example, a catalyst and the N-substituted azetidine-2-carboxylic acid compound represented by the formula (1) are usually added to a solvent, and a hydrogen gas is thereafter supplied into the reaction system. The supply of the hydrogen gas may be carried out by passing the gas through the reaction system or the reaction system may be stirred under a hydrogen gas atmosphere at normal pressure or compressed pressure.

When a reducing agent other than hydrogen is employed, for example, the optically active N-substituted azetidine-2-carboxylic acid compound represented by the formula (1) and a catalyst may be added to a solvent and the reducing agent may thereafter be added to the mixture.

The reaction temperature is usually within a range of from −50° C. to 200° C., preferably from 0° C. to 150° C.

When the substituent $R^2$ is an acyl group in the optically active N-substituted azetidine-2-carboxylic acid compound represented by the formula (1), the optically active azetidine-2-carboxylic acid represented by the formula (3) can be easily obtained by heating the above acid compound in an aqueous solution of an inorganic acid such as hydrogen chloride and hydrogen bromide. Alternatively, the optically active azetidine-2-carboxylic acid represented by the formula (3) can also be obtained by using a deacylation enzyme such as acylase in the presence of water.

When the substituent $R^2$ is an alkyloxycarbonyl group in the optically active N-substituted azetidine-2-carboxylic acid compound represented by the formula (1), the optically active azetidine-2-carboxylic acid represented by the formula (3) can be obtained by reacting the above acid compound under an acidic condition by using hydrochloric acid, sulfuric acid, trifluoroacetic acid or the like in water or an organic solvent, and heating if necessary.

When the substituent $R^2$ is an allyloxycarbonyl group in the optically active N-substituted azetidine-2-carboxylic acid compound represented by the formula (1), the optically active azetidine-2-carboxylic acid represented by the formula (3) can be obtained, for example, by using tri-n-butyltin hydride, acetic acid and the like in the presence of a catalyst such as tetrakis(triphenylphosphine)palladium.

When the substituent $R^2$ is an allyl group in the optically active N-substituted azetidine-2-carboxylic acid compound represented by the formula (1), the optically active azetidine-2-carboxylic acid represented by the formula (3) can be obtained by contacting the above acid compound with thiosalicylic acid at room temperature or elevated temperature in a solvent such as tetrahydrofuran in the presence of a catalyst prepared, for example, from bis (dibenzylidene acetone)palladium and 1, 4-bis (diphenylphosphino)butane.

When the substituent $R^2$ is a sulfonyl group in the optically active N-substituted azetidine-2-carboxylic acid compound represented by the formula (1), the optically active azetidine-2-carboxylic acid represented by the formula (3) can be obtained by reacting the above acid compound under an acidic condition by using hydrochloric acid, sulfuric acid acetic acid, trifluoroacetic acid or the like and heating if necessary, or by means of Birch reduction.

After completion of the above-mentioned reactions, the optically active azetidine-2-carboxylic acid represented by the formula (3) can be readily obtained by means of a conventional after-treating method such as a method wherein, after separating a catalyst by filtration, the filtrate is condensed and a method wherein, after extraction, the extracted solution is condensed. The product may be further purified by means of recrystallization, column chromatography and the like, if necessary.

According to the process of the present invention, the optically active N-substituted azetidine-2-carboxylic acid compound represented by the formula (1) can be produced by a single step in a good optical purity, and the compound of the (1) can be readily converted to the optically active azetidine-2-carboxylic acid represented by the formula (3).

EXAMPLES

The following Examples further illustrate the present invention in detail, but are not to be construed limiting the present invention thereto.

Example 1

Into a 500 ml Erlenmeyer flask was added 100 ml of a liquid medium which was a part of a medium prepared by dissolving 5 g of glycerol, 6 g of yeast extract, 9 g of potassium phosphate monobasic and 4 g of potassium phosphate dibasic in 1 liter of water and adjusting the pH value to 7.0, and the liquid medium was sterilized. After that, ampicillin was added to the medium so that the content thereof became 50 μg/ml, and 1 loop-full microorganism was inoculated from a slant culture of the esterase gene recombinant microorganism which was derived from Arthrobacter SC-6-98-28 strain prepared by the method described in Reference Example 1, and culture was carried out with rotary shaking at 30° C. for 24 hours. Next, into a 3 liter Jar-fermenter (manufactured by Marubishi Bioengi Co., Ltd., Model MDL) was fed with 1500 ml of sterilized liquid medium comprising 15 g of glycerol, 25 g of yeast extract, 0.4 g of potassium phosphate monobasic, 2 g of magnesium sulfate and 0.1 g of ferrous sulfate per 1 liter of water and adjusting the pH value to 7.0, and then 15 ml of the liquid medium above-incubated in the Erlenmeyer flask was inoculated thereto. Aerobic culture with stirring was commenced at 30° C., and in the middle of a logarithmic growth phase (at the time 10 to 15 hours after the beginning of the culture), IPTG (isopropylthio-β-D-galactoside) was added so that a final concentration thereof became 1 mM. The sterilized medium was thereafter fed and the culture was continued for 40 hours in total to give a culture broth of microorganism.

Example 2

To a racemic mixture of methyl N-(R)-phenylethylazetidine-2-carboxylic acid ester (200 mg) was added 1.8 ml of t-butyl methyl ether at 20° C. to 25° C. After stirring the mixture for one minute, 20 μl of the culture broth of microorganism prepared according to Example 1 was suspended in 2 ml of a 100 mM phosphate buffer (pH 7.0) and poured into the above mixture. The resultant mixture was heated to 40° C. and stirred for 8 hours. After standing, the mixture was separated into an organic layer and an aqueous layer. According to the analysis of the aqueous layer by means of a high-performance liquid chromatography (column: SUMIPAX ODS-212, 6 mmφ×15 cm, manufactured by Sumika Chemical Analysis Service, Ltd.), [N-(R)-phenylethyl]azetidine-2-carboxylic acid was obtained with a conversion ratio of 38.1% and an R-isomer ratio of 98.7%.

Example 3

To a racemic mixture of methyl N-(S)-phenylethylazetidine-2-carboxylic acid ester (200 mg) was added 1.8 ml of t-butyl methyl ether at 20° C. to 25° C. After stirring the mixture for one minute, 20 μl of the culture broth of microorganism prepared according to Example 1 was suspended in 2 ml of a 100 mM phosphate buffer (pH 7.0) and poured into the above mixture. The resultant mixture was heated to 40° C. and stirred for 8 hours. After standing, the mixture was separated into an organic layer and an aqueous layer. According to the analysis of the aqueous layer by means of a high-performance liquid chromatography (column: SUMIPAX ODS-212, 6 mm$\phi$×15 cm, manufactured by Sumika Chemical Analysis Service, Ltd.), [N-(S)-phenylethyl]azetidine-2-carboxylic acid was obtained with a conversion ratio of 18.1% and an R-isomer ratio of 92.1%.

Example 4

To a racemic mixture of ethyl N-benzylazetidine-2-carboxylic acid ester (200 mg) was added 1.8 ml of t-butyl methyl ether at 20° C. to 25° C. After stirring the mixture for one minute, 20 $\mu$l of the culture broth of microorganism prepared according to Example 1 was suspended in 2 ml of a 100 mM phosphate buffer (pH 7.0) and poured into the above mixture. The resultant mixture was heated to 40° C. and stirred for 8 hours. After standing, the mixture was separated into an organic layer and an aqueous layer. According to the analysis of the aqueous layer by means of a high-performance liquid chromatography (column: SUMICHIRAL OA-3100, 4.6 mm$\phi$×25 cm, manufactured by Sumika Chemical Analysis Service, Ltd.), N-benzylazetidine-2-carboxylic acid was obtained with a conversion ratio of 46.3% and an R-isomer ratio of 96.4%.

Example 5

To 2 ml of a 100 mM phosphate buffer (pH 7.0) was added 20 $\mu$l of the culture broth of microorganism prepared according to Example 1 at 20° C. to 25° C. After stirring the mixture for one minute, a racemic mixture of methyl N-(R)-phenylethylazetidine-2-carboxylic acid ester (200 mg) was added to the mixture. The resultant mixture was heated to 40° C. and stirred for 2 hours. After standing, the mixture was separated into an organic layer and an aqueous layer. According to the analysis of the aqueous layer by means of a high-performance liquid chromatography (column: SUMIPAX ODS-212, 6 mm$\phi$×15 cm, manufactured by Sumika Chemical Analysis Service, Ltd.), [N-(R)-phenylethyl] azetidine-2-carboxylic acid was obtained with a conversion ratio of 49.3% and an R-isomer ratio of 95.6%.

Example 6

To 2 ml of a 100 mM phosphate buffer (pH 7.0) was added 20 $\mu$l of the culture broth of microorganism prepared according to Example 1 at 20° C. to 25° C. After stirring the mixture for one minute, a racemic mixture of methyl N-(S)-phenylethylazetidine-2-carboxylic acid ester (200 mg) was added to the mixture. The resultant mixture was heated to 40° C. and stirred for 2 hours. After standing, the mixture was separated into an organic layer and an aqueous layer. According to the analysis of the aqueous layer by means of a high-performance liquid chromatography (column: SUMIPAX ODS-212, 6 mm$\phi$×15 cm, manufactured by Sumika Chemical Analysis Service, Ltd.), [N-(S)-phenylethyl] azetidine-2-carboxylic acid was obtained with a conversion ratio of 50.3% and an R-isomer ratio of 87.0%.

Example 7

To 2 ml of a 100 mM phosphate buffer (pH 7.0) was added 20 $\mu$l of the culture broth of microorganism prepared according to Example 1 at 20° C. to 25° C. After stirring the mixture for one minute, a racemic mixture of methyl N-benzylazetidine-2-carboxylic acid ester (200 mg) was added to the mixture. The resultant mixture was heated to 40° C. and stirred for 2 hours. After standing, the mixture was separated into an organic layer and an aqueous layer. According to the analysis of the aqueous layer by means of a high-performance liquid chromatography (column: SUMICHIRAL OA-3100, 4.6 mm$\phi$×25 cm, manufactured by Sumika Chemical Analysis Service, Ltd.), N-benzylazetidine-2-carboxylic acid was obtained with a conversion ratio of 58.8% and an R-isomer ratio of 77.6%.

Example 8

A culture broth of microorganism was obtained, in the same manner as that described in Example 1, by culturing the esterase gene recombinant microorganism derived from Chromobacterium SC-YM-1 strain prepared by the method described in Reference Example 2.

Example 9

To a racemic mixture of methyl N-(R)-phenylethylazetidine-2-carboxylic acid ester (22 mg) was added 1 ml of t-butyl methyl ether at 20° C. to 25° C. After stirring the mixture for one minute, 2 $\mu$l of the culture broth of microorganism prepared according to Example 8 was suspended in 1 ml of a 100 mM phosphate buffer (pH 7.0) and poured into the above mixture. The resultant mixture was heated to 40° C. and stirred for 6 hours. After standing, the mixture was separated into an organic layer and an aqueous layer. According to the analysis of the aqueous layer by means of a high-performance liquid chromatography (column: SUMIPAX ODS-212, 6 mm$\phi$×15 cm, manufactured by Sumika Chemical Analysis Service, Ltd.), [N-(R)-phenylethyl] azetidine-2-carboxylic acid was obtained with a conversion ratio of 31.4% and an S-isomer ratio of 68.5%.

Example 10

To 3 ml of a sterilized medium including 1.0% of glucose, 0.7% of peptone, 0.5% of yeast extract and 0.2% of dipotassium hydrogenphosphate in a test tube with a diameter of 18 mm was added 4 $\mu$l of tributyrin, and thereafter 100 $\mu$l of a culture of Arthrobacter sp. ATCC21908 strain previously cultured with linearly shaking for 3 days at 30° C. in the same medium was added. The mixture was subjected to cultivation with linearly shaking for 1 day at 30° C. to produce respective cultured cells. To respective 0.5 ml of the cultured cells were added 1 ml of t-butyl methyl ether in which 21.5 mg of ethyl N-benzylazetidine-2-carboxylic acid ester was dissolved and 0.5 ml of 200 mM phosphate buffer (pH 7.0). The resultant mixture was linearly shaken at 40° C. for 16 hours. After standing, an aqueous layer separated was analyzed by means of a high-performance liquid chromatography (column: SUMICHIRAL OA-3100, 4.6 mm$\phi$×25 cm, manufactured by Sumika Analysis Service, Ltd.) and it was found that N-benzylazetidine-2-carboxylic acid was obtained with a conversion ratio of 24.8% and an R-isomer ratio of 96.6%.

Example 11

To the aqueous N-benzylazetidine-2-carboxylic acid solution obtained in Example 4 is added 170 mg of 10% Pd(OH)$_2$ (containing water with a content of 43%) at room temperature. The mixture is stirred in an atmosphere of hydrogen gas at room temperature for 18 hours, and thereafter heated to 40° C. and stirred for another 34 hours. After this, the mixture is filtered to provide a solution of azetidine- 2-carboxylic acid as a filtrate. According to the analysis of the solution by means of a high-performance liquid chromatography (column: SUMICHIRAL OA-6000, 4.6 mmφ× 15 cm, manufactured by Sumika Chemical Analysis Service, Ltd.), the R-isomer of optically active azetidine-2-carboxylic acid is obtained.

Reference Example 1

The esterase gene recombinant microorganism which was derived from the Arthrobacter SC-6-98-28 strain (FERM BP-3658) used in Example 1 was prepared in accordance with the method described in Japanese Patent Kokai Publication No. 56787/1993.

Namely, in accordance with the method of Example described in Japanese Patent Kokai Publication No. 56787/1993, Plasmid pAGE-1 having an esterase gene derived from Arthrobacter SC-6-98-28 strain was prepared. A translational region encoding esterase was isolated from Plasmid pAGE-1 by the digestion with the restriction enzymes NspV and HindIII. The translational region encoding esterase was subjected to a ligation with a DNA fragment which was synthesized in order to convert the initiation codon GTG of an esterase gene into ATG and the expression vector pUC 118 manufactured by Takara Shuzo Co., Ltd. having a lac promoter digested with the restriction enzymes BamHI and HindIII. Thus, an expression plasmid for $E.\ coli$ having, downstream of the lac promoter, an esterase gene derived from Arthrobacter SC-6-98-28 strain was prepared, and the expression plasmid was transformed into $E.\ coli$ 05 in accordance with a conventional method to construct the recombinant microorganism.

Reference Example 2

The esterase gene recombinant microorganism derived from Chromobacterium SC-YM-1 strain used in Example 8 was prepared in accordance with the method described in Japanese Patent Kokai Publication No. 213280/1995. Namely, plasmid pCC160A189Y363term containing a gene obtained by introducing a site-specific mutation into an esterase gene derived from Chromobacterium SC-YM- 1 strain (FERM BP-6703), and the plasmid was introduced into $E.\ coli$ JM105 to construct the recombinant microorganism.

The construction method of plasmid pCC160A189Y363term will be described below.

(1) Preparation of Plasmid pCC160A

A wild-type esterase gene derived from Chromobacterium SC-YM-1 strain was first prepared in accordance with the methods described in Examples 1 to 5 in Japanese Patent Kokai Publication No. 213280/1995. Using a plasmid pCC101 (0.5 μg) as a template DNA in accordance with the method described in Japanese Patent Kokai Publication No. 213280/1995, a DNA fragment was amplified by means of a GeneAmp PCR Reagent kit manufactured by Takara Shuzo Co., Ltd. using a mutant primer MY-1 (100 pmol) represented by SEQ ID No. 27 described in the above publication and a mutant primer 160A (100 pmol) represented by SEQ ID No. 11, both mutant primer being prepared in accordance with the method described in Example 6 of the above publication. The PCR product obtained (270 bp DNA fragment) was purified using a SUPREC-02 column manufacture by Takara Shuzo Co., Ltd.

In the next step, using the plasmid pCC101 (0.5 μg) as a template DNA in the same manner as the above, a DNA fragment was amplified by means of the GeneAmp PCR Reagent kit manufactured by Takara Shuzo Co., Ltd. using a mutant primer RV-C (50 pmol) represented by SEQ ID No. 26 described in the above publication and the above-purified 270 bp DNA fragment (50 pmol) as primers. The amplified DNA fragment was digested with restriction enzymes CelIII and ClaI, and a sample was subjected to electrophoresis with 4% agarose gel (NuSieve3:1Agarose manufactured by Takara Shuzo Co., Ltd.), and about 240 bp of a DNA fragment was then isolated and purified by using a GeneClean DNA purification kit (Bio101, manufactured by Inc).

Additionally, the plasmid pCC101 (3 μg) was digested with the restriction enzymes CelIII and ClaI, and treated with alkaline phosphatase. The obtained DNA fragment (4.2 kbp) and about 240 bp of the previously prepared, mutant-introduced DNA fragment were connected with each other using a DNA ligation kit manufactured by Takara Shuzo Co., Ltd., and the resultant was transformed into $E.\ coli$ JM109 in accordance with a conventional method.

The plasmid pCC 160A was prepared from the transformant obtained above in accordance with a conventional method. Determining the base sequence of the mutated portion of the plasmid by the dideoxy method confirmed that mutation was introduced as designed.

(2) Preparation of Plasmid pCC 189Y

A plasmid pCC 189Y was prepared in the same manner as in the preparation of the plasmid pCC160A, except for changing the mutant primer 160A used in the preparation of pCC160A to a mutant primer 189Y represented by SEQ ID No. 24 which was prepared according to the method described in Example 6. Determining the base sequence of the mutated portion of the plasmid by the dideoxy method confirmed that mutaion was introduced as designed.

(3) Preparation of Plasmid pCC363term

Using the plasmid pCC101 (0.5 μg) as a template DNA, a DNA fragment was amplified by means of the GeneAmp PCR Reagent kit manufactured by Takara Shuzo Co., Ltd. using a mutant primer MY-2 (100 pmol) represented by SEQ ID No. 30 and a mutant primer A363term (100 pmol) represented by SEQ ID No. 28. The PCR product obtained (150 bp fragment) was purified using a SUPREC-02 column manufacture by Takara Shuzo Co., Ltd. In the next step, using the plasmid pCC101 (0.5 μg) as a template DNA in the same manner as the above, a DNA fragment was amplified by means of the GeneAmp PCR Reagent kit manufactured by Takara Shuzo Co., Ltd. using a mutant primer RV-D (50 pmol) represented by SEQ ID No. 29 and the above-purified 150 bp DNA fragment (50 pmol) as primers. The amplified DNA fragment was digested with restriction enzymes BstPI and XbaI, and a sample was subjected to electrophoresis with 4% agarose gel (NuSieve3:1Agarose manufactured by Takara Shuzo Co., Ltd.), and about 280 bp of a DNA fragment was then isolated and purified by using the GeneClean DNA purification kit (Bio101, manufactured by Inc). Additionally, the plasmid pCC101 (3 μg) was digested with the restriction enzymes BstPI and XbaI, and treated with alkaline phosphatase. The obtained DNA fragment (4.2 kbp) and 280 bp of the previously prepared, mutant-introduced DNA fragment were connected with each other using the DNA ligation kit manufactured by Takara Shuzo Co., Ltd., and the resultant was transformed into $E.\ coli$ JM109 in accordance with a conventional method. The plasmid pCC363term was prepared from the transformant obtained above in accordance with a conventional method. Determining the base sequence of the mutated portion of the plasmid by the dideoxy method confirmed that mutation was introduced as designed.

(4) Construction of Multimutation-Type Esterase-Producing Plasmid

Three kinds of DNA fragments, namely 0.6 kbp of a DNA fragment obtained by digesting the mutant plasmid pCC160A (10 μg) obtained in the above (1) with restriction enzymes EcoRI and FspI, 0.4 kbp of a fragment obtained by digesting the mutant plasmid pCC189Y (10 μg) obtained in the above (2) with restriction enzymes FspI and BstPI, and 3.4 kbp of a DNA fragment obtained by digesting the mutant plasmid pCC363term (3 μg) obtained in the above (3) with restriction enzymes BstPI and EcoRI, were connected together using the DNA ligation kit manufactured by Takara Shuzo Co., Ltd. The resultant was transformed into *E. coli* JM105 in accordance with a conventional method to obtain a transformant containing a plasmid pCC160A189Y363term having a multimutation-type esterase gene.

What is claimed is:

1. A process for producing an optically active N-substituted azetidine-2-carboxylic acid compound represented by the formula (1):

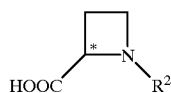

(1)

wherein $R^2$ represents:

an aralkyl group, which may be substituted on its aromatic ring with at least one group selected from an alkyl group having 1 to 8 carbon atoms, an alkoxy group having 1 to 8 carbon atoms, a halogen atom and a nitro group, or an alkylcarbonyl group having 1 to 8 carbon atoms, which may be substituted with at least one group selected from an alkoxy group having 1 to 8 carbon atoms, a halogen atom and a nitro group, or an arylcarbonyl group, which may be substituted on its aromatic ring with at least one group selected from an alkyl group having 1 to 8 carbon atoms, an alkoxy group having 1 to 8 carbon atoms, a halogen atom, a phenyl group and a nitro group, or an alkyloxycarbonyl group having 1 to 8 carbon atoms, which may be substituted with at least one group selected from a halogen atom, a sulfonyl group and an aryl group, which aryl group may be substituted on its aromatic ring with at least one group selected from an alkyl group having 1 to 8 carbon atoms, an alkoxy group having 1 to 8 carbon atoms, a halogen atom and a nitro group, or an allyloxycarbonyl group, or an aryloxycarbonyl group, which may be substituted on its aromatic ring with at least one group selected from an alkyl group having 1 to 8 carbon atoms, an alkoxy group having 1 to 8 carbon atoms, a halogen atom and a nitro group, or an alkyl group having 1 to 8 carbon atoms, which may be substituted with at least one group selected from an alkoxy group having 1 to 8 carbon atoms, a halogen atom and a nitro group, or an allyl group, or an aryl group, which may be substituted on its aromatic ring with at least one group selected from an alkyl group having 1 to 8 carbon atoms, an alkoxy group having 1 to 8 carbon atoms, a halogen atom and a nitro group, or an arylsulfonyl group, which may be substituted on its aromatic ring with at least one group selected from an alkyl group having 1 to 8 carbon atoms, an alkoxy group having 1 to 8 carbon atoms, a halogen atom and a nitro group, and

* represents an asymmetric carbon atom, the process comprising asymmetrically hydrolyzing an N-substituted azetidine-2-carboxylic acid ester compound represented by the following formula (2):

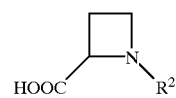

(2)

wherein $R^1$ represents:

an alkyl group having 1 to 8 carbon atoms, which may be substituted with at least one group selected from an alkoxy group having 1 to 8 carbon atoms, a halogen atom and a nitro group, or an allyl group, or an aralkyl group, which may be substituted, on its aromatic ring with at least one group selected from an alkyl group having 1 to 8 carbon atoms, an alkoxy group having 1 to 8 carbon atoms, a halogen atom and a nitro group, or an aryl group, which may be substituted on its aromatic ring with at least one group selected from an alkyl group having 1 to 8 carbon atoms, an alkoxy group having 1 to 8 carbon atoms, a halogen atom and a nitro group, and $R^2$ has the same meaning as defined above, by contacting the same with an enzyme derived from a microorganism selected from Arthrobacter SC-6-98-28 strain, Arthrobacter sp. ATCC21908 strain, Chromobacterium SC-YM-1 strain, and a mutant thereof.

2. The process according to claim 1, wherein in the N-substituted azetidine-2-carboxylic acid ester compound represented by the formula (2), $R^2$ represents an aralkyl group, which may be substituted on its aromatic ring with at least one group selected from an alkyl group having 1 to 8 carbon atoms, an alkoxy group having 1 to 8 carbon atoms, a halogen atom and a nitro group or an alkyloxycarbonyl group having 1 or 2 carbon atoms which may be substituted with an aryl group, which aryl group may be substituted on its aromatic ring with at least one group selected from an alkyl group having 1 to 8 carbon atoms, an alkoxy group having 1 to 8 carbon atoms, a halogen atom and a nitro group.

3. The process according to claim 2, wherein in the N-substituted azetidine-2-carboxylic acid ester compound represented by the formula (2), $R^1$ represents an alkyl group having 1 to 8 carbon atoms.

4. The process according to claim 1, 2 or 3, wherein the enzyme is an esterase derived from Arthrobacter SC-6-98-28 strain.

5. The process according to claim 1, 2 or 3, wherein the enzyme is an esterase produced by a recombinant microorganism transformed by introduction of a gene there into encoding an esterase derived from Arthrobacter SC-6-98-28 strain.

6. The process according to claim 1, 2 or 3, wherein the enzyme is an esterase derived from Chromobacterium SC-YM-1 strain.

7. The process according to claim 1, 2 or 3, wherein the enzyme is an esterase produced by a recombinant microorganism transformed by introduction of a gene there into encoding an esterase derived from Chromobacterium SC-YM-1 strain.

8. The process according to claim 1, 2 or 3, wherein the process is carried out in the presence of an organic solvent.

9. A process
according to claim 1, which process further comprises eliminating the N-substituent of an optically active N-substituted azetidine-2-carboxylic acid compound of the following formula (2):

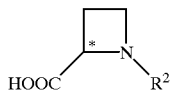
(2)

wherein $R^2$ represents:

an aralkyl group, which may be substituted on its aromatic ring with at least one group selected from an alkyl group having 1 to 8 carbon atoms, an alkoxy group having 1 to 8 carbon atoms, a halogen atom and a nitro group, or an alkylcarbonyl group having 1 to 8 carbon atoms, which may be substituted with at least one group selected from an alkoxy group having 1 to 8 carbon atoms, a halogen atom and a nitro group, or an arylcarbonyl group, which may be substituted on its aromatic ring with at least one group selected from an alkyl group having 1 to 8 carbon atoms, an alkoxy group having 1 to 8 carbon atoms, a halogen atom, a phenyl group and a nitro group, or an alkyloxycarbonyl group having 1 to 8 carbon atoms, which may be substituted with at least one group selected from a halogen atom, a sulfonyl group and an aryl group, which aryl group may be substituted on its aromatic ring with at least one group selected from an alkyl group having 1 to 8 carbon atoms, an alkoxy group having 1 to 8 carbon atoms, a halogen atom and a nitro group, or an allyloxycarbonyl group, or an aryloxycarbonyl group, which may be substituted on its aromatic ring with at least one group selected from an alkyl group having 1 to 8 carbon atoms, an alkoxy group having 1 to 8 carbon atoms, a halogen atom and a nitro group, or an alkyl group having 1 to 8 carbon atoms, which may be substituted with at least one group selected from an alkoxy group having 1 to 8 carbon atoms, a halogen atom and a nitro group, or an allyl group, or an aryl group, which may be substituted on its aromatic ring with at least one group selected from an alkyl group having 1 to 8 carbon atoms, an alkoxy group having 1 to 8 carbon atoms, a halogen atom and a nitro group, or an arylsulfonyl group, which may be substituted on its aromatic ring with at least one group selected from an alkyl group having 1 to 8 carbon atoms, an alkoxy group having 1 to 8 carbon atoms, a halogen atom and a nitro group, and

* represents an asymmetric carbon atom, to produce an optically active azetidine-2-carodylic acid represented by the formula (3):

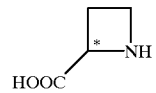
(3)

wherein * represents an asymmetric carbon atom.

10. The process according to claim 9, wherein $R^2$ represents:

an aralkyl group, which may be substituted on its aromatic ring with at least one group selected from an alkyl group having 1 to 8 carbon atoms, an alkoxy group having 1 to 8 carbon atoms, a halogen atom and a nitro group or an alkyloxycarbonyl group having 1 or 2 carbon atoms, which may be substituted with an aryl group, which aryl group may be substituted on its aromatic ring with at least one group selected from an alkyl group having 1 to 8 carbon atoms, an alkoxy group having 1 to 8 carbon atoms, a halogen atom and a nitro group, and the elimination reaction is conducted by reacting the N-substituent of the optically active N-substituted azetidine-2-carboxylic acid compound of the formula (2) with a reducing agent in the presence of a noble metal catalyst.

11. The process according to claim 10, wherein the reducing agent is hydrogen, or hydrazine or a salt thereof, or formic acid or a salt thereof.

* * * * *